(12) United States Patent
Morgenthau

(10) Patent No.: US 11,413,260 B2
(45) Date of Patent: *Aug. 16, 2022

(54) USE OF 1,3-PROPANEDISULFONIC ACID OR PHARMACEUTICALLY ACCEPTABLE SALTS THEREOF FOR THE TREATMENT OF SARCOIDOSIS

(71) Applicant: Icahn School of Medicine at Mount Sinai, New York, NY (US)

(72) Inventor: Adam S. Morgenthau, New York, NY (US)

(73) Assignee: ICAHN SCHOOL OF MEDICINE AT MOUNT SINAI, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 16/903,064

(22) Filed: Jun. 16, 2020

(65) Prior Publication Data
US 2021/0030701 A1 Feb. 4, 2021

Related U.S. Application Data

(63) Continuation of application No. 16/246,231, filed on Jan. 11, 2019, now Pat. No. 10,682,321, which is a (Continued)

(51) Int. Cl.
*A61K 31/185* (2006.01)
*A61K 45/06* (2006.01)
(Continued)

(52) U.S. Cl.
CPC .......... *A61K 31/185* (2013.01); *A61K 9/0053* (2013.01); *A61K 45/06* (2013.01);
(Continued)

(58) Field of Classification Search
CPC .... A61K 31/185; A61K 45/06; A61K 9/0053; A61K 9/005
See application file for complete search history.

(56) References Cited

U.S. PATENT DOCUMENTS

| 7,253,306 B2 | 8/2007 | Kong et al. |
| 8,322,886 B1 | 12/2012 | Bowser |

(Continued)

FOREIGN PATENT DOCUMENTS

| CN | 101528216 | 9/2009 |
| EP | 3137071 | 1/2019 |

(Continued)

OTHER PUBLICATIONS

CA2,947,159, "Office Action", dated May 12, 2021, 3 pages.
(Continued)

*Primary Examiner* — Savitha M Rao
(74) *Attorney, Agent, or Firm* — Kilpatrick Townsend & Stockton LLP

(57) ABSTRACT

The present disclosure relates to methods for the treatment of sarcoidosis. In certain aspects and embodiments, the disclosure provides compositions containing 1,3-propanedisulfonic acid or a pharmaceutically acceptable salt thereof and/or the use of such compositions for the treatment of Sarcoidosis. In another aspect, the disclosure relates to compositions containing 1,3-propanedisulfonic acid or a pharmaceutically acceptable salt thereof plus a second active agent. In yet another aspect, the disclosure relates to kits containing agents useful for the treatment of sarcoidosis.

15 Claims, 1 Drawing Sheet

Protocol

THP-1  $5 \times 10^5$ cells/ml

| PMA | SAA | KIACTA |
|---|---|---|
| 200ng/ml → | 10ug/ml + | 0 ~ 10 mg/ml |
| 48hr | 24hr | 24hr |

PMA = phorbol 12-myristate 13-acetate (EMD Cat.# 524400)
SAA = serum amyloid A (PeroTech Cat.#300-13)
KIACTA C933 (NRA610-01-CF)

ELISA Kit
IL-18; MBL Cat.#7620
IL-10; invitrogen Cat.#KHC0101
TNF; BD Cat.#550610

Related U.S. Application Data continuation of application No. 15/335,289, filed on Oct. 26, 2016, now abandoned, which is a continuation of application No. PCT/US2015/028336, filed on Apr. 29, 2015.

(60) Provisional application No. 61/986,719, filed on Apr. 30, 2014.

(51) Int. Cl.
| | |
|---|---|
| A61K 9/00 | (2006.01) |
| A61P 1/02 | (2006.01) |
| A61P 1/16 | (2006.01) |
| A61P 1/00 | (2006.01) |
| A61P 9/00 | (2006.01) |
| A61P 1/18 | (2006.01) |

(52) U.S. Cl.
CPC .............. *A61P 1/00* (2018.01); *A61P 1/02* (2018.01); *A61P 1/16* (2018.01); *A61P 1/18* (2018.01); *A61P 9/00* (2018.01)

(56) References Cited

U.S. PATENT DOCUMENTS

| 8,372,886 B2 | 2/2013 | Hauck et al. |
| 2006/0252829 A1 | 11/2006 | Garceau et al. |
| 2012/0208850 A1 | 8/2012 | Kong et al. |
| 2016/0252829 A1 | 9/2016 | Kawahara et al. |

FOREIGN PATENT DOCUMENTS

| JP | 2008535906 | 9/2008 |
| WO | 0027807 | 5/2000 |
| WO | 2015168315 | 11/2015 |
| WO | 2016023911 | 2/2016 |
| WO | 2017070003 | 4/2017 |

OTHER PUBLICATIONS

CN201910051673.2, "Office Action", Dec. 3, 2020, 19 pages.
JP2019-211209, "Office Action", dated Mar. 30, 2021, 7 pages.
Wenjing et al., "Therapeutics of Chinese and Western Medicine for Autoimmune Diseases", Military Medical Science Press, Jan. 31, 2005.
Baha et al., "A Case of Sarcoidosis Associated With Anti-Tumor Necrosis Factor Treatment", Journal of Investigative Medicine High Impact Case Reports, © 2015 American Federation for Medical Research, 2015, pp. 1-5.
Baughman et al., "Sarcoidosis", The Lancet, vol. 361, No. 9363, Mar. 29, 2003, pp. 1111-1118.
Drent et al., "Consequences of Sarcoidosis", 2015, 11 pages.
EP15786643.5, "Extended European Search Report", Sep. 29, 2017, 10 pages.
Ex Parte Gleave, "Appeal No. 2012-009281 (P.T.A.B. Jan. 29, 2014)".
Manenti et al., "Eprodisate in Amyloid A Amyloidosis: A Novel Therapeutic Approach?", Expert Opinion on Pharmacotherapy, vol. 9, No. 12, Aug. 1, 2008, pp. 2175-2180.
Obici et al., "AA Amyloidosis: Basic Knowledge, Unmet Needs and Future Treatments", Swiss Medical Weekly, vol. 142, No. 5, May 31, 2012, 8 pages.
PCT/US2015/028336, "International Preliminary Report on Patentability", dated Nov. 10, 2016, 7 pages.
PCT/US2015/028336, "International Search Report and Written Opinion", dated Jul. 31, 2015, 14 pages.
SG11201608906S, "Written Opinion", dated Aug. 15, 2017, 4 pages.
Valeyre et al., "Sarcoidosis", Available Online at: http://www.thelancet.com/pdfs/journals/lancet/ PIIS0140-6736(13)60680-7.pdf, Oct. 1, 2013, pp. 1157-1167.
U.S. Appl. No. 15/335,289, "Advisory Action", dated Jan. 24, 2019, 3 pages.
AU2015253163, "First Examination Report", dated Jun. 29, 2019, 4 pages.
Baughman et al., "Inhibitors of Tumor Necrosis Factor (TNF) in Sarcoidosis: Who, What, and How to Use Them", Sarcoidosis Vasculitis and Diffuse Lung Diseases, vol. 25, No. 2, 2008, pp. 76-89.
Chen et al., "Serum Amyloid A Regulates Granulomatous Inflammation in Sarcoidosis Through Toll-Like Receptor-2", American Journal of Respiratory and Critical Care Medicine, vol. 181, No. 4, 2010, pp. 360-373.
IL248428, "Office Action", dated May 14, 2019, 4 pages.
JP2016-565303, "Office Action", dated Jan. 8, 2019, 5 pages.
JP2016-565303, "Office Action", dated Jul. 23, 2019, 7 pages.
Judson, "The Treatment of Pulmonary Sarcoidosis", Respiratory Medicine, vol. 106, No. 10, Oct. 2012, pp. 1351-1361.
Manenti et al., "Eprodisate in Amyloid A Amyloidosis: A Novel Therapeutic Approach?", Expert Opin.Pharmacother., vol. 9, Issue 12, 2008, pp. 2175-2180.
MX/A/2016/014261, "Office Action", dated Jul. 3, 2019, 3 pages.
U.S. Appl. No. 16/246,231, "Non-Final Office Action", dated Jul. 18, 2019, 12 pages.
U.S. Appl. No. 16/246,231, "Notice of Allowance", dated Feb. 11, 2020, 10 pages.
BR1120160252446, Office Action, dated Jun. 30, 2020, 4 pages.
MX/A/2016/014261, "Notice of Allowance", dated Aug. 11, 2020, 3 pages.
JP2019-211209, "Office Action" with English Translation, dated Oct. 13, 2020, 8 pages.
JP2019-211209, "Notice of Decision to Grant" with Machine Translation, dated Sep. 14, 2021, 5 pages.
"Clinical Surgery of Chinese and Western Medicine", China Medical Science Press, Jan. 31, 2002, 2 pages.
"Overview of Rheumatism", American Arthritis Foundation, Dec. 31, 1988, 4 pages.
AE1129/2016, "First Examination Report and Search Report", dated Oct. 19, 2021, 11 pages.
CN201910051673.2, "Office Action", dated Sep. 28, 2021, 20 pages.
EA201692196, "Office Action", dated Sep. 8, 2021, 3 pages.
CA2,947,159, "Notice of Allowance", dated Mar. 29, 2022, 1 page.
CN201910051673.2, "Office Action", dated Mar. 2, 2022, 13 pages.
EA201692196, "Notice of Decision to Grant", dated Mar. 3, 2022, 3 pages.

Protocol

THP-1  5 x 10⁵ cells/ml

| PMA | SAA | KIACTA |
|---|---|---|
| 200ng/ml → | 10ug/ml + | 0 ～ 10 mg/ml |
| 48hr | 24hr | 24hr |

PMA = phorbol 12-myristate 13-acetate (EMD Cat.# 524400

SAA = serum amyloid A (PeroTech Cat.#300-13)

KIACTA C933 (NRA610-01-CF)

ELISA Kit

IL-18; MBL Cat.#7620

IL-10; invitrogen Cat.#KHC0101

TNF; BD Cat.#550610

USE OF 1,3-PROPANEDISULFONIC ACID OR PHARMACEUTICALLY ACCEPTABLE SALTS THEREOF FOR THE TREATMENT OF SARCOIDOSIS

CROSS-REFERENCES TO RELATED APPLICATIONS

This application is a continuation of U.S. application Ser. No. 16/246,231, filed on Jan. 11, 2019, which is a continuation of U.S. application Ser. No. 15/335,289, filed on Oct. 26, 2016, which claims priority from International Application No. PCT/US2015/028336, filed on Apr. 29, 2015, which claims priority to U.S. application Ser. No. 61/986,719, filed on Apr. 30, 2014, which are hereby incorporated by reference in their entirety.

FIELD OF THE INVENTION

The present disclosure relates to methods for the treatment of sarcoidosis.

BACKGROUND OF THE INVENTION

PCT patent application publication WO 2007/004072 discloses methods of treating AA amyloidosis by administering 1,3 propanedisulfonic acid. PCT patent application publication WO 2007/0238788 discloses methods of treating diabetic neuropathy by administering 1,3 propanedisulfonic acid.

Sarcoidosis is a rare condition that causes small patches of red and swollen tissue, called granulomas that can develop in multiple organs in the body, but mostly the lungs and skin. Corticosteroids, the mainstay of therapy in sarcoidosis, nonspecifically suppress chronic granulomatous inflammation, often causing debilitating adverse effects but do not correct the underlying disease.

SUMMARY OF THE INVENTION

In various aspects and embodiments of the present disclosure, provided are methods for treating a subject with sarcoidosis, that include administering to said subject an effective amount of 1,3-propanedisulfonic acid or a pharmaceutically acceptable salt thereof as well as relevant compositions for use in such methods. In certain embodiments, the 1,3-propanedisulfonic acid or pharmaceutically acceptable salt thereof is 1,3-propanedisulfonic acid. In certain embodiments of the disclosure, the 1,3-propanedisulfonic acid or pharmaceutically acceptable salt thereof is the disodium salt of 1,3-propanedisulfonic acid.

In some embodiments of the disclosure, the subject being treated has chronic sarcoidosis (as opposed to acute sarcoidosis). In certain embodiments of the disclosure the subject being treated has acute sarcoidosis.

In various embodiments of the disclosure, sarcoidosis may affect one or more of the lungs, liver, heart, nervous system (including the brain), skin, lymph glands, musculoskeletal system (e.g, bones, joints, muscles), spleen, eyes, sinuses, nasal mucosa, larynx, the gastrointestinal tract, reproductive organs, salivary glands and/or kidneys.

In certain embodiments of the disclosure, sarcoidosis specifically affects the lungs.

In some embodiments, the administration of 1,3-propanedisulfonic acid or pharmaceutically acceptable salt thereof results in the reduction in one or more inflammatory mediators selected from the group consisting of IL-18, IL-10 and TNF.

In some embodiments, the administration of 1,3-propanedisulfonic acid or pharmaceutically acceptable salt thereof results in the reduction and/or alleviation of sarcoidosis symptoms in the subject (e.g., granuloma formation, granulomatous inflammation, and the like).

In certain embodiments of the disclosure, the effective amount of 1,3-propanedisulfonic acid or pharmaceutically acceptable salt thereof comprises administration of at least 1 mg/kg thereof to said subject per dose.

In certain embodiments of the disclosure, the effective amount of 1,3-propanedisulfonic acid or pharmaceutically acceptable salt thereof is administered more than once daily. Exemplary administration protocols contemplate administration of 1,3-propanedisulfonic acid or pharmaceutically acceptable salt thereof at least 2 times daily; at least 3 times daily; at least 4 times daily; at least 5 times daily; at least 6 times daily; or even more frequently, including continuous administration thereof. In certain embodiments the 1,3-propanedisulfonic acid is administered to a subject (for example orally) in a dose of 400 mg, or 800 mg, or 1,200 mg per administration. In some embodiments the 1,3-propanedisulfonic acid is administered to a subject in a dose of 400 mg QID, or 600 mg QID, or 800 mg QID, or 1000 mg QID, or 1,200 mg QID per administration.

In certain embodiments of the disclosure, no more than 20 mg/kg of 1,3-propanedisulfonic acid or pharmaceutically acceptable salt thereof is administered to said subject per dose.

1,3-propanedisulfonic acid or pharmaceutically acceptable salts thereof can be administered in a variety of ways, e.g., by oral, parenteral, intraperitoneal, intraspinal, intracerebral, nasal, mucosal, transdermal, intravascular, intraarterial, intramuscular, or subcutaneous delivery, or the like.

In certain embodiments of the disclosure, 1,3-propanedisulfonic acid or pharmaceutically acceptable salts thereof are administered by oral delivery.

In certain embodiments of the disclosure, there are provided pharmaceutically acceptable compositions for the treatment of sarcoidosis, said compositions comprising 1,3-propanedisulfonic acid or a pharmaceutically acceptable salt thereof and a pharmaceutically acceptable carrier therefor.

In certain embodiments of the disclosure, the above-described pharmaceutically acceptable compositions may further comprise a second agent traditionally employed for the treatment of sarcoidosis. An exemplary second agent is a corticosteroid.

BRIEF DESCRIPTION OF THE FIGURE

FIG. 1 summarizes the protocol employed to evaluate the effect of 1,3-propanedisulfonic acid (or a pharmaceutically acceptable salt thereof) on SAA (serum amyloid A) stimulated inflammation in THP-1 cells.

DETAILED DESCRIPTION OF THE INVENTION

In accordance with the present disclosure, there are provided methods for treating a subject with sarcoidosis, said method comprising administering to said subject an effective amount of 1,3-propanedisulfonic acid or a pharmaceutically acceptable salt thereof.

The term "subject" includes living organisms in which sarcoidosis or a related disease can occur, or which are susceptible to sarcoidosis or related diseases. The term "subject" includes animals (e.g., mammals, e.g., cats, dogs, horses, pigs, cows, goats, sheep, rodents, e.g., mice or rats, rabbits, squirrels, bears, primates (e.g., chimpanzees, monkeys, gorillas, and humans)), as well as chickens, ducks, peking ducks, geese, and transgenic species thereof. The term "subject," includes to a subject, e.g., a human, specifically chosen to receive 1,3-propanedisulfonic acid or a pharmaceutically acceptable salt thereof, or a composition containing same. Accordingly, in some embodiments, subjects include subjects who are at risk of or have been diagnosed with sarcoidosis. Subjects at risk of developing sarcoidosis include those with an underlying disease, such as an inflammatory disease, infection, hereditary fever or neoplasm. In some embodiments, a preferred subject is a human.

The terms "treatment" or "treating" of a subject includes the application or administration of 1,3-propanedisulfonic acid or a pharmaceutically acceptable salt thereof, or a composition containing same to a subject (or application or administration of 1,3-propanedisulfonic acid or a pharmaceutically acceptable salt thereof to a cell or tissue from a subject) with the purpose of stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indicia of success in the treatment or amelioration of an injury, pathology or condition, including any objective or subjective parameter such as abatement; remission; lessening of the rate of worsening; stabilization, diminishing of symptoms or making the injury, pathology or condition more tolerable to the subject; slowing in the rate of degeneration or decline; making the final point of degeneration less debilitating; or improving a subject's physical or mental well-being. In an embodiment, the term "treating" can include increasing a subject's life expectancy.

The term "therapeutically effective amount" refers to the amount of a compound which is effective to treat a subject, e.g., treat a subject for sarcoidosis or a related disease or treat a subject having an underlying disease, such as, but not limited to, an inflammatory disorder, a malignant neoplasm, or chronic microbial infection. The therapeutically effective amount may vary based on the particular disorder(s) the subject is suffering from, the age, weight, and lifestyle of a particular subject. In addition, the therapeutically effective amount may depend on the severity of the disease state, organ function, kidney function, or underlying disease (e.g., the subject may be suffering from an inflammatory disease, a malignant neoplasm, a chronic infection).

The dosage administered in the methods of the present disclosure may be selected such that desired pharmacokinetic parameters and/or biologically favorable parameters are obtained after administration of the compound of the disclosure to the subject. In one embodiment, the dosage is selected such that the subject receives at least 1 mg/kg of 1,3-propanedisulfonic acid or a pharmaceutically acceptable salt thereof per dose; in another embodiment, the dosage is selected such that the subject receives at least 2 mg/kg of 1,3-propanedisulfonic acid or a pharmaceutically acceptable salt thereof per dose; in still another embodiment, the dosage is selected such that the subject receives at least 3 mg/kg of 1,3-propanedisulfonic acid or a pharmaceutically acceptable salt thereof per dose; in yet another embodiment, the dosage is selected such that the subject receives at least 4 mg/kg of 1,3-propanedisulfonic acid or a pharmaceutically acceptable salt thereof per dose; in a still further embodiment, the dosage is selected such that the subject receives at least 5 mg/kg of 1,3-propanedisulfonic acid or a pharmaceutically acceptable salt thereof per dose; in some embodiments, the dosage is selected such that the subject receives at least 6 mg/kg of 1,3-propanedisulfonic acid or a pharmaceutically acceptable salt thereof per dose; in some embodiments, the dosage is selected such that the subject receives at least 7 mg/kg of 1,3-propanedisulfonic acid or a pharmaceutically acceptable salt thereof per dose; in some embodiments, the dosage is selected such that the subject receives at least 8 mg/kg of 1,3-propanedisulfonic acid or a pharmaceutically acceptable salt thereof per dose; in some embodiments, the dosage is selected such that the subject receives at least 9 mg/kg of 1,3-propanedisulfonic acid or a pharmaceutically acceptable salt thereof per dose; in some embodiments, the dosage is selected such that the subject receives at least 10 mg/kg of 1,3-propanedisulfonic acid or a pharmaceutically acceptable salt thereof per dose; in some embodiments, the dosage is selected such that the subject receives at least 15 mg/kg of 1,3-propanedisulfonic acid or a pharmaceutically acceptable salt thereof per dose. In some embodiments, no more than 20 mg/kg of 1,3-propanedisulfonic acid or pharmaceutically acceptable salt thereof is administered to said subject per dose.

In a further embodiment, the disclosure also pertains, at least in part, to a pharmaceutical formulation. The formulation comprises an active agent which is 1,3-propane disulfonic acid or a pharmaceutically acceptable salt thereof in an amount effective to treat or prevent sarcoidosis, and a pharmaceutically acceptable carrier. In one embodiment, the formulation is orally administered to a subject having sarcoidosis in a dose of 400 mg of 1,3-propanedisulfonic acid or a pharmaceutically acceptable salt thereof. In another embodiment, the formulation is orally administered to a subject having sarcoidosis in a dose of 800 mg of 1,3-propane disulfonic acid or a pharmaceutically acceptable salt thereof, and a pharmaceutically acceptable carrier. In yet another embodiment, the formulation is orally administered to a subject having sarcoidosis in a dose of 1200 mg of 1,3-propane disulfonic acid or a pharmaceutically acceptable salt thereof, and a pharmaceutically acceptable carrier.

In a further embodiment, the disclosure pertains to a pharmaceutical formulation comprising 1,3-propane disulfonic acid or a pharmaceutically acceptable salt thereof, and a pharmaceutically acceptable carrier for oral administration to a subject having sarcoidosis for twenty-four months in a dose of 400 mg of the active agent; or in a dose of 800 mg of the active agent; or in a dose of 1200 mg of the active agent.

In another embodiment, the disclosure also pertains to a pharmaceutical formulation, comprising 1,3-propane disulfonic acid or a pharmaceutically acceptable salt thereof, and a pharmaceutically acceptable carrier, wherein the formulation is orally administered for seven days in a dose of 400 mg QID of the active agent; or in a dose of 800 mg QID of the active agent; or in a dose of 1200 mg QID of the active agent; or in a dose of 1600 mg QID of the active agent; or in a dose of 2000 mg QID of the active agent.

In another further embodiment, the disclosure also pertains to a method of stabilizing or improving renal function or delaying progression of renal disease in a subject having sarcoidosis. The method includes orally administering an effective amount of a formulation comprising 1,3-propane-disulfonic acid or a pharmaceutically acceptable salt thereof and one or more pharmaceutically acceptable carriers.

In another embodiment, the disclosure pertains to a method of treating or preventing sarcoidosis in a subject.

The method includes administering to a subject in need thereof, a therapeutically effective amount of 1,3-propanedisulfonic acid or a pharmaceutically acceptable salt thereof, in combination with a second agent, such that AA amyloidosis is treated or prevented.

The term "in combination with" refers to the concurrent administration of 1,3-propanedisulfonic acid or a pharmaceutically acceptable salt thereof and a second agent; the administration of 1,3-propanedisulfonic acid or a pharmaceutically acceptable salt thereof can be carried out prior to administration of the second agent; or administration of the second agent can be carried out prior to administration of 1,3-propanedisulfonic acid or a pharmaceutically acceptable salt thereof.

The compounds of the present disclosure contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of 1,3-propanedisulfonic acid.

These salts can likewise be prepared in situ during the final isolation and purification of the agents, or by separately reacting the purified agent in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

"Pharmaceutically acceptable salts" also includes, for example, derivatives of agents modified by making base salts thereof, as described further below and elsewhere in the present application. Examples of pharmaceutically acceptable salts include alkali or organic salts of acidic residues such as sulfonates. Pharmaceutically acceptable salts include the conventional non-toxic salts or the quaternary ammonium salts of the parent agent formed, for example, from non-toxic inorganic or organic acids. Such conventional non-toxic salts include those derived from inorganic acids such as hydrochloric, hydrobromic, sulfuric, sulfamic, phosphoric, and nitric acid; and the salts prepared from organic acids such as acetic, propionic, succinic, glycolic, stearic, lactic, malic, tartaric, citric, ascorbic, palmoic, maleic, hydroxymaleic, phenylacetic, glutamic, mesylate, benzoic, salicylic, sulfanilic, 2-acetoxybenzoic, fumaric, toluenesulfonic, methanesulfonic, ethane disulfonic, oxalic, and isethionic acid. Pharmaceutically acceptable salts may be synthesized from the parent agent which contains a basic or acidic moiety by conventional chemical methods. Generally, such salts may be prepared by reacting the free acid or base forms of these agents with a stoichiometric amount of the appropriate base or acid in water or in an organic solvent, or in a mixture of the two.

All acid, salt, base, and other ionic and non-ionic forms of the compounds described are included as compounds of the disclosure. For example, if a compound is shown as an acid herein, the salt forms of the compound are also included. Likewise, if a compound is shown as a salt, the acid and/or basic forms are also included.

In another embodiment, the disclosure pertains to a pharmaceutical formulation for treating sarcoidosis, comprising a therapeutically effective amount of 1,3-propanedisulfonic acid or a pharmaceutically acceptable salt thereof in a formulation such that the formulation has at least one favorable biological property (FBP) upon administration to a subject.

The term "pharmaceutical formulation" includes pharmaceutical compositions as described below. In a further embodiment, the pharmaceutical formulations are designed to have favorable biological properties which enhance the ability of the compounds of the disclosure to treat sarcoidosis and/or related diseases. The favorable biological properties of the formulation were discovered by administering the compounds of the disclosure to subjects during clinical trials.

The disclosure also pertains, at least in part, to a pharmaceutical composition comprising a therapeutically effective amount of 1,3-propanedisulfonic acid or a pharmaceutically acceptable salt thereof and second agent. In a further embodiment, the therapeutically effective amount is effective to treat sarcoidosis.

In a further embodiment, the disclosure pertains to a packaged pharmaceutical composition. The packaged pharmaceutical composition includes a therapeutically effective amount of 1,3-propanedisulfonic acid or a pharmaceutically acceptable salt thereof packaged in combination with a label or insert advising that the composition be administered in combination with a second agent. In a further embodiment, the therapeutically effective amount is effective to treat sarcoidosis.

In yet another further embodiment, the disclosure pertains to a packaged pharmaceutical composition, which includes a therapeutically effective amount of a second agent packaged in combination with a label or insert advising that the composition be administered in combination with 1,3-propanedisulfonic acid or a pharmaceutically acceptable salt thereof.

The term "label or insert" includes, but is not limited to all written, electronic, or spoken communication with the subject, or with any person substantially responsible for the care of the subject, regarding the administration of the compositions of the present disclosure. An insert may further include information regarding coadministration of the compositions of the present disclosure with other compounds or compositions, e.g., second agents. Additionally, an insert may include instructions regarding administration of the compositions of the present disclosure without food.

In yet another embodiment, the disclosure pertains to a packaged pharmaceutical composition, which includes a container holding a pharmaceutical composition comprising a therapeutically effective amount of 1,3-propanedisulfonic acid or a pharmaceutically acceptable salt thereof in combination with a label or insert advising that the composition be administered without food.

1,3-propanedisulfonic acid or a pharmaceutically acceptable salt thereof may be supplied in a solution with an appropriate solvent or in a solvent-free form (e.g., lyophilized). In another aspect of the disclosure, the agents and buffers necessary for carrying out the methods of the disclosure may be packaged as a kit. The kit may be commercially used according to the methods described herein and may include instructions for use in a method of the disclosure. Additional kit components may include acids, bases, buffering agents, inorganic salts, solvents, antioxidants, preservatives, or metal chelators. The additional kit components are present as pure compositions, or as aqueous or organic solutions that incorporate one or more additional kit components. Any or all of the kit components optionally further comprise buffers.

1,3-propanedisulfonic acid or a pharmaceutically acceptable salt thereof may also be administered in a variety of ways, e.g., parenterally, intraperitoneally, intraspinally, intracerebrally, and the like. Dispersions can be prepared in glycerol, liquid polyethylene glycols, and mixtures thereof and in oils. Under ordinary conditions of storage and use, these preparations may contain a preservative to prevent the growth of microorganisms.

To administer 1,3-propanedisulfonic acid or a pharmaceutically acceptable salt thereof by other than parenteral administration, it may be necessary to coat the active agent with, or co-administer the active agent with, a material to prevent its inactivation. For example, 1,3-propanedisulfonic acid or a pharmaceutically acceptable salt thereof may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., *J. Neuroimmunol.* 7, 27 (1984)). It should be noted that the term "pharmaceutical composition" includes the "pharmaceutical formulations" described above.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi.

Suitable pharmaceutically acceptable vehicles include, without limitation, any non-immunogenic pharmaceutical adjuvants suitable for oral, parenteral, nasal, mucosal, transdermal, intravascular (IV), intraarterial (IA), intramuscular (IM), and subcutaneous (SC) administration routes, such as phosphate buffer saline (PBS).

The vehicle can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, isotonic agents are included, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic agent in the required amount in an appropriate solvent with one or a combination of ingredients enumerated above, as required, followed by filtered sterilization. Generally, dispersions are prepared by incorporating the therapeutic agent into a sterile vehicle which contains a basic dispersion medium and the required other ingredients from those enumerated above. In the case of sterile powders for the preparation of sterile injectable solutions, the methods of preparation are vacuum drying and freeze-drying which yields a powder of the active ingredient (i.e., the compound of the disclosure) plus any additional desired ingredient from a previously sterile-filtered solution thereof.

1,3-propanedisulfonic acid or a pharmaceutically acceptable salt thereof can be orally administered, for example, with an inert diluent or an assimilable edible carrier. 1,3-propanedisulfonic acid or a pharmaceutically acceptable salt thereof and other ingredients may also be enclosed in a hard or soft shell gelatin capsule, compressed into tablets, or incorporated directly into the subject's diet. For oral therapeutic administration, 1,3-propanedisulfonic acid or a pharmaceutically acceptable salt thereof may be incorporated with excipients and used in the form of ingestible tablets, buccal tablets, troches, capsules, elixirs, suspensions, syrups, wafers, and the like. The percentage of the 1,3-propanedisulfonic acid or a pharmaceutically acceptable salt thereof in the compositions and preparations may, of course, be varied. The amount of 1,3-propanedisulfonic acid or a pharmaceutically acceptable salt thereof in such therapeutically useful compositions is such that a suitable dosage will be obtained.

The present disclosure therefore includes pharmaceutical formulations comprising 1,3-propanedisulfonic acid or a pharmaceutically acceptable salt thereof, in pharmaceutically acceptable vehicles for aerosol, oral and parenteral administration. Also, the present disclosure includes such compounds, or salts thereof, which have been lyophilized and which may be reconstituted to form pharmaceutically acceptable formulations for administration, as by intravenous, intramuscular, or subcutaneous injection. Administration may also be intradermal or transdermal.

In accordance with the present disclosure, 1,3-propanedisulfonic acid or a pharmaceutically acceptable salt thereof may be administered orally or through inhalation as a solid, or may be administered intramuscularly or intravenously as a solution, suspension or emulsion. Alternatively, the agents or salts may also be administered by inhalation, intravenously or intramuscularly as a liposomal suspension.

Pharmaceutical compositions or formulations are also provided which are suitable for administration as an aerosol, by inhalation. These formulations comprise a solution or suspension of 1,3-propanedisulfonic acid or a pharmaceutically acceptable salt thereof, or a plurality of solid particles of the agent or salt. The desired formulation may be placed in a small chamber and nebulized. Nebulization may be accomplished by compressed air or by ultrasonic energy to form a plurality of liquid droplets or solid particles comprising the agents or salts. The liquid droplets or solid particles should have a particle size in the range of about 0.5 to about 5 microns. The solid particles can be obtained by processing the solid agent of 1,3-propanedisulfonic acid or a pharmaceutically acceptable salt thereof, in any appropriate manner known in the art, such as by micronization. The size of the solid particles or droplets will be, for example, from about 1 to about 2 microns. In this respect, commercial nebulizers are available to achieve this purpose.

A pharmaceutical formulation suitable for administration as an aerosol may be in the form of a liquid, the formulation will comprise a water-soluble form of 1,3-propanedisulfonic acid or a pharmaceutically acceptable salt thereof, in a carrier which comprises water. A surfactant may be present which lowers the surface tension of the formulation sufficiently to result in the formation of droplets within the desired size range when subjected to nebulization.

Peroral compositions also include liquid solutions, emulsions, suspensions, and the like. The pharmaceutically acceptable vehicles suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, tragacanth, and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Pharmaceutical compositions may also be coated by conventional methods, typically with pH or time-dependent coatings, such that the subject agent is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, waxes, and shellac.

Other compositions useful for attaining systemic delivery of 1,3-propanedisulfonic acid or a pharmaceutically acceptable salt thereof include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

1,3-propanedisulfonic acid or a pharmaceutically acceptable salt thereof can also be administered topically to a subject, e.g., by the direct laying on or spreading of a composition containing same on the epidermal or epithelial tissue of the subject, or transdermally via a "patch". Such compositions include, for example, lotions, creams, solutions, gels and solids. These topical compositions may comprise an effective amount, usually at least about 0.1 wt %, or even from about 1 wt % to about 5 wt %, of 1,3-propanedisulfonic acid or a pharmaceutically acceptable salt thereof. Suitable carriers for topical administration typically remain in place on the skin as a continuous film, and resist being removed by perspiration or immersion in water. Generally, the carrier is organic in nature and capable of having dispersed or dissolved therein the therapeutic agent. The carrier may include pharmaceutically acceptable emollients, emulsifiers, thickening agents, solvents and the like.

Toxicity and therapeutic efficacy of such agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and can be expressed as the ratio LD50/ED50, and usually a larger therapeutic index is more efficacious. While compounds that exhibit toxic side effects may be used, care should be taken to design a delivery system that targets such agents to the site of affected tissue in order to minimize potential damage to unaffected cells and, thereby, reduce side effects.

It is understood that appropriate doses depend upon a number of factors within the ken of the ordinarily skilled physician, veterinarian, or researcher. The dose(s) of 1,3-propanedisulfonic acid or a pharmaceutically acceptable salt thereof will vary, for example, depending upon the identity, size, and condition of the subject or sample being treated, further depending upon the route by which the composition is to be administered, if applicable, and the effect which the practitioner desires the 1,3-propanedisulfonic acid or a pharmaceutically acceptable salt thereof to have upon the subject. Exemplary doses include milligram or microgram amounts of 1,3-propanedisulfonic acid or a pharmaceutically acceptable salt thereof per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses depend upon the potency. Such appropriate doses may be determined using the assays known in the art. When 1,3-propanedisulfonic acid or a pharmaceutically acceptable salt thereof is to be administered to an animal (e.g., a human), a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, and any drug combination.

For subjects having sarcoidosis, doses may depend on the state of renal function in the subject, as measured, for example, by the rate of creatinine clearance, which may affect the rate of clearance of the compound from the subject. In this case, subjects with a lower rate of creatinine clearance would be expected to achieve a particular plasma concentration at a lower dose than those with a higher rate of creatinine clearance.

Parenteral compositions may be formulated in dosage unit form for ease of administration and uniformity of dosage. Dosage unit form as used herein refers to physically discrete units suited as unitary dosages for the subjects to be treated; each unit containing a predetermined quantity of 1,3-propanedisulfonic acid or a pharmaceutically acceptable salt thereof calculated to produce the desired therapeutic effect in association with the required pharmaceutical vehicle. The specifications for the dosage unit forms of the disclosure are dictated by and directly dependent on (a) the unique characteristics of the therapeutic agent and the particular therapeutic effect to be achieved, and (b) the limitations inherent in the art of compounding 1,3-propanedisulfonic acid or a pharmaceutically acceptable salt thereof for the treatment of sarcoidosis or related disease.

Various aspects of the present disclosure are illustrated by the following non-limiting examples. The examples are for illustrative purposes and are not a limitation on any practice of the present disclosure. It will be understood that variations and modifications can be made without departing from the spirit and scope of the disclosure. One of ordinary skill in the art readily knows how to synthesize or commercially obtain the reagents and components described herein.

Those skilled in the art will recognize, or be able to ascertain using no more than routine experimentation, numerous equivalents to the specific procedures, embodiments, claims, and examples described herein. Such equivalents are considered to be within the scope of this disclosure and covered by the claims appended hereto. The contents of all references, issued patents, and published patent applications cited throughout this application are hereby incorporated by reference. The disclosure is further illustrated by the following example, which should not be construed as further limiting.

Example 1

THP-1 cells were subjected to PMA (phorbol 12-myristate 13-acetate (EMD Cat. #524400)), SAA (serum amyloid A (PeroTech Cat. #300-13)), and 1,3-propanedisulfonic acid (KIACTA C933 (NRA610-01-CF)). The protocol is summarized in FIG. 1. The SAA treated cells were used as a positive control, with the SAA increasing the inflammatory mediators, TNF, IL-18 and IL-10. 1,3-propanedisulfonic acid is added to the cell cultures and the effect on TNF, IL-18 and IL-10 levels is measured.

Example 2

In the protocol described in Example 1, 1,3-propanedisulfonic acid at a concentration of 5 mg/ml and above inhibits SAA-induced production of the inflammatory mediator, IL-18 by the THP-1 cells.

In the protocol described in Example 1, 1,3-propanedisulfonic acid at a concentration of 2.5 mg/ml and above inhibits SAA-induced production of the inflammatory mediator, IL-10 by the THP-1 cells.

In the protocol described in Example 1, 1,3-propanedisulfonic acid at a concentration of 1.25 mg/ml and above inhibits SAA-induced production of the inflammatory mediator, IL-TNF by the THP-1 cells.

Example 3

A patient is diagnosed with sarcoidosis, and 1,3-propane disulfonic acid is administered to the patient. The treatment results in the reduction and/or alleviation of sarcoidosis symptoms in the patient.

Various modifications of the present disclosure, in addition to those shown and described herein, will be apparent to those skilled in the art of the above description. Such modifications are also intended to fall within the scope of the appended claims.

Patents and publications mentioned in the specification are indicative of the levels of those skilled in the art to which the disclosure pertains. These patents and publications are incorporated herein by reference to the same extent as if each individual application or publication was specifically and individually incorporated herein by reference.

The foregoing description is illustrative of particular embodiments of the disclosure, but is not meant to be a limitation upon the practice thereof. The following claims, including all equivalents thereof, are intended to define the scope of any the invention described herein.

That which is claimed is:

1. A method for treating a subject with sarcoidosis, said method comprising administering to said subject an effective amount of 1,3-propanedisulfonic acid or a pharmaceutically acceptable salt thereof.

2. The method of claim 1 wherein said subject has chronic sarcoidosis.

3. The method of claim 1 wherein said sarcoidosis affects the subject's lungs, liver, heart, nervous system, skin, lymph glands, musculoskeletal system, spleen, eyes, sinuses, nasal mucosa, larynx, the gastrointestinal tract, reproductive organs, salivary glands and/or kidneys.

4. The method of claim 3 wherein said sarcoidosis affects the subject's lungs.

5. The method of claim 1 wherein at least 1 mg/kg of 1,3-propanedisulfonic acid or pharmaceutically acceptable salt thereof is administered to said subject per dose.

6. The method of claim 5 wherein said 1,3-propanedisulfonic acid or pharmaceutically acceptable salt thereof is administered more than once daily.

7. The method of claim 5 wherein said 1,3-propanedisulfonic acid or pharmaceutically acceptable salt thereof is administered 2, 3, 4, 5 or 6 times daily.

8. The method of claim 5 wherein no more than 20 mg/kg of 1,3-propanedisulfonic acid or pharmaceutically acceptable salt thereof is administered to said subject per dose.

9. The method of claim 1 wherein said 1,3-propanedisulfonic acid or pharmaceutically acceptable salt thereof is administered by oral, parenteral, intraperitoneal, intraspinal, intracerebral, nasal, mucosal, transdermal, intravascular, intraarterial, intramuscular, or subcutaneous delivery.

10. The method of claim 1 wherein said 1,3-propanedisulfonic acid or pharmaceutically acceptable salt thereof is administered by oral delivery.

11. The method of claim 1 wherein said 1,3-propanedisulfonic acid or pharmaceutically acceptable salt thereof is 1,3-propanedisulfonic acid.

12. The method of claim 1 wherein said 1,3-propanedisulfonic acid or pharmaceutically acceptable salt thereof is a disodium salt of 1,3-propanedisulfonic acid.

13. The method of claim 1, wherein treating the subject with sarcoidosis comprises reducing or alleviating a sarcoidosis symptom.

14. The method of claim 13, wherein the sarcoidosis symptom that is reduced or alleviated is granuloma formation or granulomatous inflammation.

15. The method of claim 1, wherein said sarcoidosis affects the subject's lungs, wherein at least 1 mg/kg and no more than 20 mg/kg of 1,3-propanedisulfonic acid or pharmaceutically acceptable salt thereof is administered to said subject per dose, and wherein treating the subject with sarcoidosis comprises reducing or alleviating granuloma formation or granulomatous inflammation.

* * * * *